US00PP15466P2

(12) United States Plant Patent
Bergman

(10) Patent No.: US PP15,466 P2
(45) Date of Patent: Jan. 4, 2005

(54) ***CHRYSANTHEMUM* PLANT NAMED 'YELLOW YOWOODSTOCK'**

(50) Latin Name: *Chrysanthemum×morifolium*
Varietal Denomination: Yellow Yowoodstock

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/787,049

(22) Filed: Feb. 25, 2004

(51) Int. Cl.[7] ..... A01H 5/00

(52) U.S. Cl. ..... Plt./295

(58) Field of Search ..... Plt./295

*Primary Examiner*—Anne Marie Grunberg
(74) *Attorney, Agent, or Firm*—C. A. Whealy

(57) ABSTRACT

A new and distinct cultivar of *Chrysanthemum* plant named 'Yellow Yowoodstock', characterized by its uniform and outwardly spreading plant habit; strong and freely branching growth habit; dark green-colored foliage; uniform flowering response and habit; can be grown as a disbud or as a spray-type; early flowering habit; large anemone-type inflorescences; yellow-colored ray florets and enlarged yellow green to yellow-colored disc florets; and good postproduction longevity with plants maintaining good substance and color for about two to three weeks in an interior environment.

2 Drawing Sheets

Botanical classification/cultivar designation: *Chrysanthemum×morifolium* cultivar Yellow Yowoodstock.

BACKGROUND OF THE INVENTION

The present Invention relates to a new and distinct cultivar of *Chrysanthemum* plant, botanically known as *Chrysanthemum×morifolium* and hereinafter referred to by the name 'Yellow Yowoodstock'.

The new *Chrysanthemum* is a product of a planned breeding program conducted by the Inventor in Fort Myers, Fla. The objective of the program is to create or discover new potted *Chrysanthemum* cultivars that are suitable for year-round production with uniform plant growth habit, good vigor and strong branching habit, numerous inflorescences, desirable inflorescence form and floret colors, fast and uniform flowering response, and good postproduction longevity.

The new *Chrysanthemum* is a naturally-occurring whole plant mutation of the *Chrysanthemum* cultivar Yowoodstock, disclosed in U.S. Plant patent application Ser. No. 10/396,576. The new *Chrysanthemum* was discovered and selected by the Inventor as a single flowering plant from within a population of flowering plants of Yowoodstock in April, 2001, in a controlled environment in Fort Myers, Fla. The selection of this plant was based on its uniform plant growth habit, good vigor and strong branching habit, numerous inflorescences, desirable inflorescence form and floret colors, fast and uniform flowering response, and good postproduction longevity.

Asexual reproduction of the new *Chrysanthemum* by vegetative tip cuttings was first conducted in Fort Myers, Fla. in July, 2001. Asexual reproduction by cuttings has shown that the unique features of this new *Chrysanthemum* are stable and reproduced true to type in successive generations.

SUMMARY OF THE INVENTION

The cultivar Yellow Yowoodstock has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Yellow Yowoodstock'. These characteristics in combination distinguish 'Yellow Yowoodstock' as a new and distinct *Chrysanthemum*:

1. Uniform and outwardly spreading plant habit.
2. Strong and freely branching growth habit.
3. Dark green-colored foliage.
4. Uniform flowering response and habit.
5. Can be grown as a disbud or as a spray-type.
6. Early flowering, eight week response time.
7. Large anemone-type inflorescences.
8. Yellow-colored ray florets and enlarged yellow green to yellow-colored disc florets.
9. Good postproduction longevity with plants maintaining good substance and color for about two to three weeks in an interior environment.

Plants of the new *Chrysanthemum* can be compared to plants of the parent, the cultivar Yowoodstock. Plants of the new *Chrysanthemum* differ from plants of the cultivar Yowoodstock primarily in ray floret coloration as plants of the cultivar Yowoodstock have white-colored ray florets.

Plants of the new *Chrysanthemum* can be compared to plants of the cultivar Yellow Blush, disclosed in U.S. Plant Pat. No. 9,455. In side-by-side comparisons conducted in Fort Myers, Fla., plants of the new *Chrysanthemum* differed from plants of the cultivar Yellow Blush primarily in inflorescence form as plants of the cultivar Yellow Blush had daisy-type inflorescences.

BRIEF DESCRIPTION OF THE PHOTOGRAPHS

The accompanying colored photographs illustrate the overall appearance of the new *Chrysanthemum* showing the colors as true as it is reasonably possible to obtain in colored reproductions of this type. Colors in the photographs may differ from the color values cited in the detailed botanical description which accurately describe the colors of the new *Chrysanthemum.*

The photograph on the first sheet comprises a side perspective view of typical flowering plants of 'Yellow Yowoodstock' grown as a spray-type.

The photograph on the second sheet comprises a close-up view of typical inflorescences of 'Yellow Yowoodstock' grown as a spray-type.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown and flowered during the winter in Salinas, Calif., in a fiberglass-covered greenhouse and under conditions which approximate those generally used in commercial potted *Chrysanthemum* production. During the production of these plants, the following conditions were measured: day temperatures, 21 to 27° C.; night temperatures, 17 to 19° C.; and light levels, 5,000 to 6,000 foot-candles. Four unrooted cuttings were directly stuck in 15-cm containers, exposed to long day/short night conditions, and pinched once about two weeks later. At the time of the pinch, the photoinductive short day/long night treatments were initiated. Plants used for the description were grown as spray-types. Measurements and numerical values represent averages of typical flowering plants.

Botanical classification: *Chrysanthemum×morifolium* cultivar Yellow Yowoodstock.

Commercial classification: Anemone-type potted *Chrysanthemum.*

Parentage: Naturally-occurring whole plant mutation of the *Chrysanthemum×morifolium* cultivar Yowoodstock, disclosed in U.S. Plant patent application Ser. No. 10/396,576.

Propagation:

*Type.*—Terminal tip cuttings.

*Time to initiate roots.*—About four days at 21° C.

*Time to produce a rooted cutting.*—About ten days at 21° C.

*Root description.*—White, close to 155D; fibrous.

*Rooting habit.*—Freely branching.

Plant description:

*Appearance.*—Herbaceous anemone-type potted *Chrysanthemum* that can be grown as a spray or as a disbud-type. Upright with lateral branches outwardly spreading; uniformly mounded crown. Strong and freely branching growth habit; about three lateral branches develop after removal of terminal apex (pinching); dense and full plants.

*Plant height.*—About 25 cm.

*Plant width.*—About 33 cm.

*Lateral branches.*—Length: About 18.5 cm. Diameter: About 4 mm. Internode length: About 1.1 cm. Strength: Strong. Texture: Pubescent. Color: Close to 144A.

*Foliage description.*—Arrangement: Alternate; simple. Length: About 8.7 cm. Width: About 5.3 cm. Apex: Mucronate. Base: Mostly truncate. Margin: Palmately lobed, sinuses between lateral lobes parallel to divergent. Texture, upper and lower surfaces: Pubescent. Color: Developing and fully expanded foliage, upper surface: Close to 147A. Developing and fully expanded foliage, lower surface: Close to 147B. Venation, upper surface: Close to 147A to 147B. Venation, lower surface: Close to 147B. Petiole length: About 2.4 cm. Petiole diameter: About 4 mm. Petiole color, upper surface: Close to 146A. Petiole color, lower surface: Close to 146B.

Inflorescence description:

*Appearance.*—Anemone-type inflorescence form with elongated oblong-shaped ray florets. Inflorescences borne on terminals above foliage. Disk and ray florets develop acropetally on a capitulum. Inflorescences not fragrant. Plants can be grown as spray or as disbud-types.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering; plants exposed to two weeks of long day/short night conditions followed by photoinductive short day/long night conditions flower about eight weeks later.

*Postproduction longevity.*—Inflorescences maintain good color and substance for about two to three weeks in an interior environment.

*Quantity of inflorescences.*—About four inflorescences develop per lateral branch.

*Inflorescence bud.*—Height: About 5 mm. Diameter: About 8 mm. Shape: Oblate. Color: Close to 144A.

*Inflorescence diameter.*—Large, about 10.2 cm.

*Inflorescence depth (height).*—About 3.4 cm.

*Diameter of disc.*—About 4 cm.

*Receptacle diameter.*—About 9 mm.

*Ray florets.*—Shape: Elongated oblong. Orientation: Initially upright, then perpendicular to the peduncle and eventually reflexing. Aspect: Straight to arching. Length: About 5 cm. Corolla tube length: About 4 mm. Width: About 8 mm. Apex: Emarginate, mucronate or acute. Base: Fused into a corolla tube. Margin: Entire. Texture: Smooth, glabrous, satiny. Number of ray florets per inflorescence: About 70 arranged in two to three whorls. Color: When opening and fully opened, upper surface: Close to 6A. When opening and fully opened, lower surface: Close to 6D.

*Disc florets.*—Arrangement: Massed at center of receptacle. Shape: Tubular, enlarged. Apex: Five-pointed. Length: About 2.3 cm. Diameter, apex: About 6 mm. Diameter, base: About 2 mm. Number of disc florets per inflorescence: About 140. Color: Immature: Close to 144A. Mature, throat: Close to 6A. Mature, tube: Close to 6D.

*Phyllaries.*—Quantity per inflorescence: About 24. Length: About 8 mm. Width: About 4 mm. Shape: Deltoid. Apex: Acute. Base: Truncate. Margin: Entire. Texture, upper surface: Waxy, smooth. Texture, lower surface: Pubescent. Color, upper surface: Close to 146A to 146B. Color, lower surface: Close to 144A.

*Peduncles.*—Length: First peduncle: About 4.5 cm. Fourth peduncle: About 7 cm. Diameter: About 2.5 mm. Angle to vertical: About 45° from vertical. Strength: Strong, flexible. Texture: Pubescent. Color: Closest to 144A.

*Reproductive organs.*—Androecium: Present on disc florets only. Anther color: Close to 12A. Pollen amount: None observed. Gynoecium: Present on both ray and disc florets. Style color: Close to 144B to 144C. Stigma color: Close to 9A.

*Seed/fruit.*—Seed and fruit production has not been observed.

Disease/pest resistance: Resistance to pathogens and pests common to *Chrysanthemums* has not been observed on plants grown under commercial greenhouse conditions.

It is claimed:

1. A new and distinct cultivar of *Chrysanthemum* plant named 'Yellow Yowoodstock', as illustrated and described.

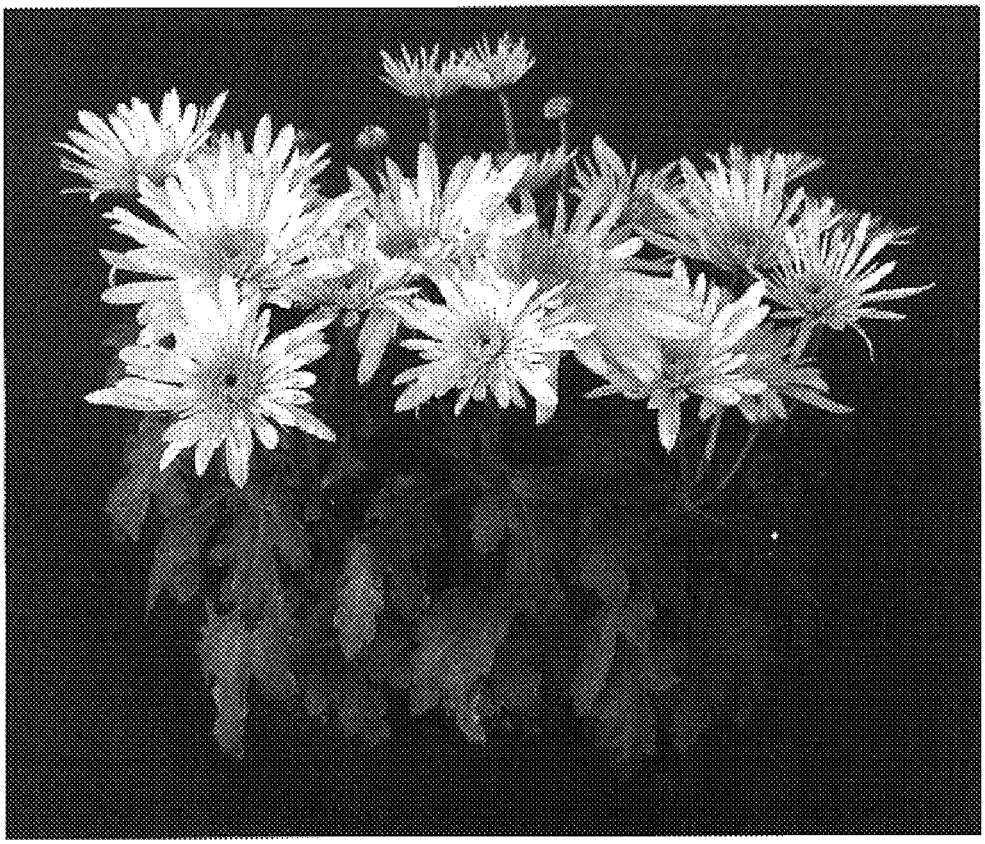

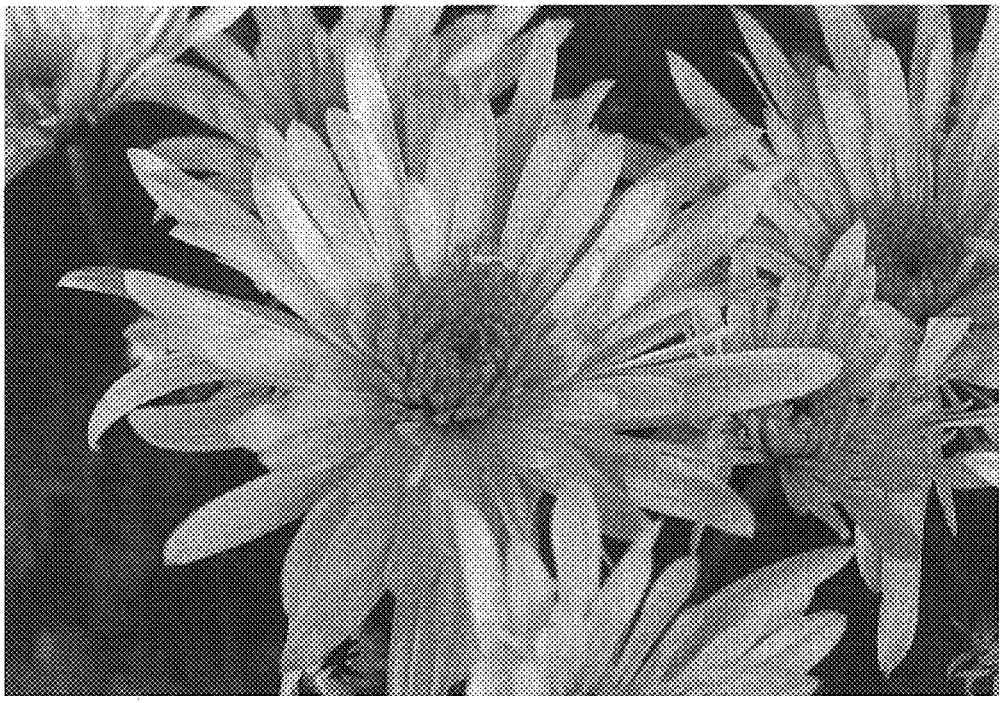

* * * * *